United States Patent
Iyer et al.

(10) Patent No.: US 11,869,633 B2
(45) Date of Patent: Jan. 9, 2024

(54) ANALYTICS AND MACHINE LEARNING FRAMEWORK FOR ACTIONABLE INTELLIGENCE FROM CLINICAL AND OMICS DATA

(71) Applicants: The Board of Trustees of the University of Illinois, Urbana, IL (US); Mayo Foundation for Medical Education and Research, Rochester, MN (US)

(72) Inventors: Ravishankar Krishnan Iyer, Champaign, IL (US); Arjun Prasanna Athreya, Urbana, IL (US); Richard Merle Weinshilboum, Rochester, MN (US); Liewei Wang, Rochester, MN (US); William Victor Bobo, Rochester, MN (US); Mark Andrew Frye, Rochester, MN (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1403 days.

(21) Appl. No.: 16/221,073

(22) Filed: Dec. 14, 2018

(65) Prior Publication Data
US 2019/0189247 A1 Jun. 20, 2019

Related U.S. Application Data

(60) Provisional application No. 62/740,199, filed on Oct. 2, 2018, provisional application No. 62/599,054, filed on Dec. 15, 2017.

(51) Int. Cl.
| | | |
|---|---|---|
| G16B 40/00 | (2019.01) | |
| G16C 20/30 | (2019.01) | |
| G16B 40/20 | (2019.01) | |
| G16B 40/30 | (2019.01) | |
| G16H 50/00 | (2018.01) | |
| G16B 20/00 | (2019.01) | |
| G16C 20/70 | (2019.01) | |

(52) U.S. Cl.
CPC ............ *G16B 40/00* (2019.02); *G16B 20/00* (2019.02); *G16B 40/20* (2019.02); *G16B 40/30* (2019.02); *G16C 20/30* (2019.02); *G16H 50/00* (2018.01); *G16C 20/70* (2019.02)

(58) Field of Classification Search
CPC ........ G16B 40/00; G16B 40/30; G16B 20/00; G16B 40/20; G16H 50/00; G16C 20/30
See application file for complete search history.

(56) References Cited

U.S. PATENT DOCUMENTS

2015/0126623 A1* 5/2015 Kawamura ............ G01N 33/50
514/789

FOREIGN PATENT DOCUMENTS

WO WO-2017210502 A1 * 12/2017 ........... G06K 9/6218

* cited by examiner

*Primary Examiner* — Jerry Lin
(74) *Attorney, Agent, or Firm* — McDonnell Boehnen Hulbert & Berghoff LLP (57) ABSTRACT

The present disclosure provides methods for accurately predicting the dynamics of symptom response to drugs or other interventions for the treatment of major depressive disorder or other psychological conditions. These methods can allow for a shortening of the time period necessary for the evaluation of a drug or other therapeutic intervention. These predictive methods are based on measured and/or self-reported symptom severity measures at two or more points in time. These measures are then discretized into symptom classes (e.g., low, moderate, severe) and the symptom classes are then applied to the predictive model to predict the progression of symptoms and/or the effectiveness of a drug or other therapeutic intervention. The predictive methods may be augmented by metabolomics data, genomics data, or other objective measures taken from a patient, allowing the use of objective physiological measures to diagnosis and treat psychological conditions heretofore diagnosed and assessed using only subjective, self-reported measures.

16 Claims, 6 Drawing Sheets

ANALYTICS AND MACHINE LEARNING FRAMEWORK FOR ACTIONABLE INTELLIGENCE FROM CLINICAL AND OMICS DATA

CROSS-REFERENCE TO RELATED APPLICATIONS

This application claims priority to U.S. Provisional Patent Application No. 62/599,054, filed Dec. 15, 2017, and U.S. Provisional Patent Application No. 62/740,199, filed Oct. 2, 2018, which are incorporated herein by reference.

STATEMENT REGARDING FEDERALLY SPONSORED RESEARCH OR DEVELOPMENT

This invention was made with government support under CNS1337732 awarded by the National Science Foundation and GM061388, GM028157, GM078233, GM092729 awarded by the National Institutes of Health. The government has certain rights in the invention.

BACKGROUND

Major depressive disorder (MDD) affects over 350 million patients worldwide. Antidepressant medications such as selective serotonin reuptake inhibitors (SSRIs) are the primary options for pharmacotherapy in adults with MDD. Pre-therapy baseline data that include 1) social and demographic data and 2) clinical data that includes the patient's response to questionnaires as assessed by a clinician may, in some conditions, be insufficient to guide clinical decision-making. Additionally, the longitudinal dynamics of symptom progression in response to beginning a course of antidepressants are not yet understood (e.g., what are the most likely changes in the symptom severity due to antidepressants taken during a trial, and what are the associated clinical outcomes at 4 weeks and 8 weeks into the trial). There are currently no widely validated biomarkers or other indicators that can be used to predict antidepressant treatment outcomes in MDD.

SUMMARY

One aspect of the present disclosure provides a method including: (i) obtaining a first symptom measure for a person, the first symptom measure corresponding to a severity of major depressive disorder at a first point in time; (ii) based on the first symptom measure, selecting a first symptom class from a first set of symptom classes, where selecting the first symptom class includes determining which symptom range of a first set of symptom ranges contains the first symptom measure and selecting the symptom class, from the first set of symptom classes, that corresponds to the determined symptom range; (iii) obtaining a second symptom measure for the person, the second symptom measure corresponding to a severity of major depressive disorder at a second point in time, where the second point in time is subsequent to the first point in time; (iv) based on the second symptom measure, selecting a second symptom class from a second set of symptom classes, where selecting the second symptom class includes determining which symptom range of a second set of symptom ranges contains the second symptom measure and selecting the symptom class, from the second set of symptom classes, that corresponds to the determined symptom range; (v) determining, based on the first symptom class and the second symptom class, that the person is likely to exhibit remission; and (vi) providing an indication that the person is likely to exhibit remission.

Another aspect of the present disclosure provides a method including: (i) obtaining a first symptom measure for a person, the first symptom measure corresponding to a severity of a symptom at a first point in time; (ii) based on the first symptom measure, selecting a first symptom class from a first set of symptom classes, where selecting the first symptom class includes determining which symptom range of a first set of symptom ranges contains the first symptom measure and selecting the symptom class, from the first set of symptom classes, that corresponds to the determined symptom range; (iii) obtaining a second symptom measure for the person, the second symptom measure corresponding to a severity of the symptom at a second point in time, where the second point in time is subsequent to the first point in time; (iv) based on the second symptom measure, selecting a second symptom class from a second set of symptom classes, where selecting the second symptom class includes determining which symptom range of a second set of symptom ranges contains the second symptom measure and selecting the symptom class, from the second set of symptom classes, that corresponds to the determined symptom range; (v) determining a clinical course of action for the person based on the first symptom class and the second symptom class; and (vi) providing an indication of the determined clinical course of action.

Yet another aspect of the present disclosure provides a method including: (i) obtaining a training dataset that includes a plurality of entries. Each entry of the dataset corresponds to a respective different person, and each entry in the training dataset includes: (a) a first symptom measure that corresponds to a severity of major depressive disorder at a first point in time; (b) a second symptom measure that corresponds to a severity of major depressive disorder at a second point in time, where the second point in time is subsequent to the first point in time; and (c) a clinical outcome that is indicative of remission of major depressive disorder at a third point in time, wherein the third point in time is subsequent to the second point in time. The method additionally includes: (ii) generating, based on the first symptom measures, a first set of symptom ranges, where each symptom range in the first set of symptom ranges corresponds to a respective symptom class from a first set of symptom classes; (iii) generating, based on the second symptom measures, a second set of symptom ranges, where each symptom range in the second set of symptom ranges corresponds to a respective symptom class from a second set of symptom classes; and (iv) based on the first symptom measures, the second symptom measures, and the clinical outcomes, generating a predictive model that predicts whether remission of major depressive disorder will occur based on a first symptom class from the first set of symptom classes and a second symptom class from the second set of symptom classes.

Yet another aspect of the present disclosure provides a method including: (i) obtaining a first symptom measure for a person, where the first symptom measure corresponds to a severity of major depressive disorder at a first point in time; (ii) based on the first symptom measure, selecting a first symptom class from a first set of symptom classes, wherein selecting the first symptom class includes determining which symptom range of a first set of symptom ranges contains the first symptom measure and selecting the symptom class, from the first set of symptom classes, that corresponds to the determined symptom range; (iii) obtaining at least one of a metabolomic property or a genomic property of the person;

(iv) selecting, based on the first symptom class and the at least one of a metabolomic property or a genomic property of the person, a drug from an enumerated list of drugs for the treatment of major depressive disorder; and (v) providing the selected drug to the person.

Yet another aspect of the present disclosure provides a method including: (i) obtaining a first symptom measure for a person, where the first symptom measure corresponds to a severity of major depressive disorder at a first point in time; (ii) based on the first symptom measure, selecting a first symptom class from a first set of symptom classes, where selecting the first symptom class includes determining which symptom range of a first set of symptom ranges contains the first symptom measure and selecting the symptom class, from the first set of symptom classes, that corresponds to the determined symptom range; (iii) obtaining a second symptom measure for the person, where the second symptom measure corresponds to a severity of major depressive disorder at a second point in time, where the second point in time is subsequent to the first point in time; (iv) based on the second symptom measure, selecting a second symptom class from a second set of symptom classes, where selecting the second symptom class includes determining which symptom range of a second set of symptom ranges contains the second symptom measure and selecting the symptom class, from the second set of symptom classes, that corresponds to the determined symptom range; (v) selecting, based on the first symptom class and the second symptom class, a drug from an enumerated list of drugs for the treatment of major depressive disorder; and (vi) providing the selected drug to the person.

These as well as other aspects, advantages, and alternatives, will become apparent to those of ordinary skill in the art by reading the following detailed description, with reference where appropriate to the accompanying drawings.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

For a variety of disorders/diseases, and corresponding treatments, the efficacy of the treatment is assessed in order to determine whether to continue the treatment (or to discontinue the treatment, e.g., in favor of an alternative treatment) and/or to modify the treatment (e.g., to adjust a dose of a drug provided as part of the treatment). In order to measure the efficacy of the treatment, the severity of a symptom of the disorder may be measured before initiating the treatment, and at one or more points in time following commencement of the treatment. A clinician can then, based on the pre-treatment and post-treatment symptom measurements, as well as measurements of side effects, decide whether to continue, modify, or discontinue the treatment and/or to take some other course of action (e.g., based on a difference between the pre-treatment symptom severity and the post-treatment symptom severity). However, a clinician's judgment may not be objective, and further the clinician may delay making a decision until receiving more information, at later time points, than is strictly necessary to make such a decision. Additionally, a clinician may experience difficulty in incorporating a multitude of patient-specific physiological measurements (e.g., a patient's multi-omic information including but not limited to genomic, transcriptomic, proteomic, or metabolomic information) or other relevant data (e.g., demographic information) into such a treatment decision.

As an illustrative example, major depressive disorder may be treated by using citalopram, escitalopram, or some other antidepressant drug. In order to assess the efficacy and/or correct dosage of a particular drug, the baseline depressive symptom severity can be assessed (e.g., using a standard clinical measure, which may include a clinical assessment) before the antidepressant is provided. The drug can then be taken at an initial dosage (determined, e.g., based on the patient's weight and demographic information) for a period of time, and the symptom severity re-assessed (e.g., using the same clinical measure(s)) at one or more points in time. Due to extended periods of wash-in for antidepressant drugs, and difficulty incorporating available confounding information (e.g., measured metabolomic information about the patient), a clinician may require many weeks in order to assess the efficacy of the drug, and to determine a future course of treatment (e.g., continuing with the drug, beginning treatment with a different drug, changing drug dosage, etc.). It may be necessary to extend the assessment to additional weeks/assessments in order for the clinician to decide on a therapeutic course of action.

The present work provides improved alternatives to these traditional methods. The present work provides methods that receive measurements of symptoms at one or more points in time (e.g., at a pre-treatment time point and, potentially, one or more time points post-treatment) and, based on this information, generate a prediction of clinical efficacy of the treatment (e.g., an estimate of the future symptom severity), generate a clinical course of action (e.g., an adjusted dosage of a drug, an alternative drug, selecting a particular drug from an enumerated list of potential drugs, a surgical or therapeutic intervention, a diet modification), or generate some other clinical course of action. These methods may additionally receive information about the metabolome, genome, transcriptome, proteome, or other multi-omic measure(s), demographics, or other information (e.g., measured physiological properties) of a patient, and may generate a clinical course of action in part on this additional information. The disclosed methods may be trained using extensive datasets.

Past attempts to use artificial neural networks or other machine learning algorithms to generate such predictions and/or clinical courses of action have failed to provide results that are reliably better than those generated by human clinicians. The present work is able to provide improved performance, in part, by assigning a clinical symptom severity measure for a particular time point (e.g., a pre-treatment time point, a time point two weeks post-treatment, a time point four weeks post-treatment) to one of a discrete set of symptom classes for the particular time point. For example, the symptom classes for a pre-treatment time point could include symptom classes corresponding to low, medium, and high symptom severity values. The determined symptom class is then applied to a factor graph or other predictive model in order to determine a clinical course of action (e.g., to predict the long-term response to a drug or other treatment, to predict which drug of an enumerated set of applicable drugs is likely to provide the best effect as regards symptom reduction and/or minimization of side effects). The predictive model is, in turn, trained on such discrete symptom class inputs, rather than the observed symptom severity measures themselves.

The methods described herein may allow treatment decisions to be made earlier, by permitting symptom measures observed at earlier time points (e.g., two weeks or four weeks after beginning treatment with a particular drug, or even before any drug is prescribed) to inform a future clinical course of action (e.g., to select a drug from an enumerated list of potential drugs, selecting a dosage of such a drug) and/or to inform a change to an ongoing clinical course of action (e.g., changing the identity of the drug used, changing a dosage of the drug, determining that the patient is not likely to enter remission due to the drug), thus shortening the time needed to determine the 'optimal' treatment for a particular patient. Additionally, these methods easily permit the addition of measured patient-specific physiological properties (e.g., blood metabolite levels, transcriptomic, proteomic, genomic, or other multi-omic information) or other information (e.g., demographic data) to improve the generation of a clinical course of action and/or to predict a patient's long-term response to a particular treatment.

Note that the term "post-treatment," as used herein, is intended to refer to time points following the beginning of a treatment. Thus, a "post-treatment" point in time could be a point in time following the provision, and later cessation, of a particular treatment. For example, a time point that is two weeks "post-treatment," where the treatment is a particular surgical intervention, refers to a time point that is two weeks after the performance of the surgical intervention. In another example, a time point that is two weeks "post-treatment," where the treatment is a daily dose of an anti-depressant drug, refers to a time point that is two weeks after the patient has begun taking the anti-depressant drug. In such an example, the treatment is still ongoing at the time point that is two weeks "post-treatment," and indeed such a treatment may continue for many weeks after the time point that is two weeks "post-treatment."

II. EXAMPLE METHODS

Figure 1:
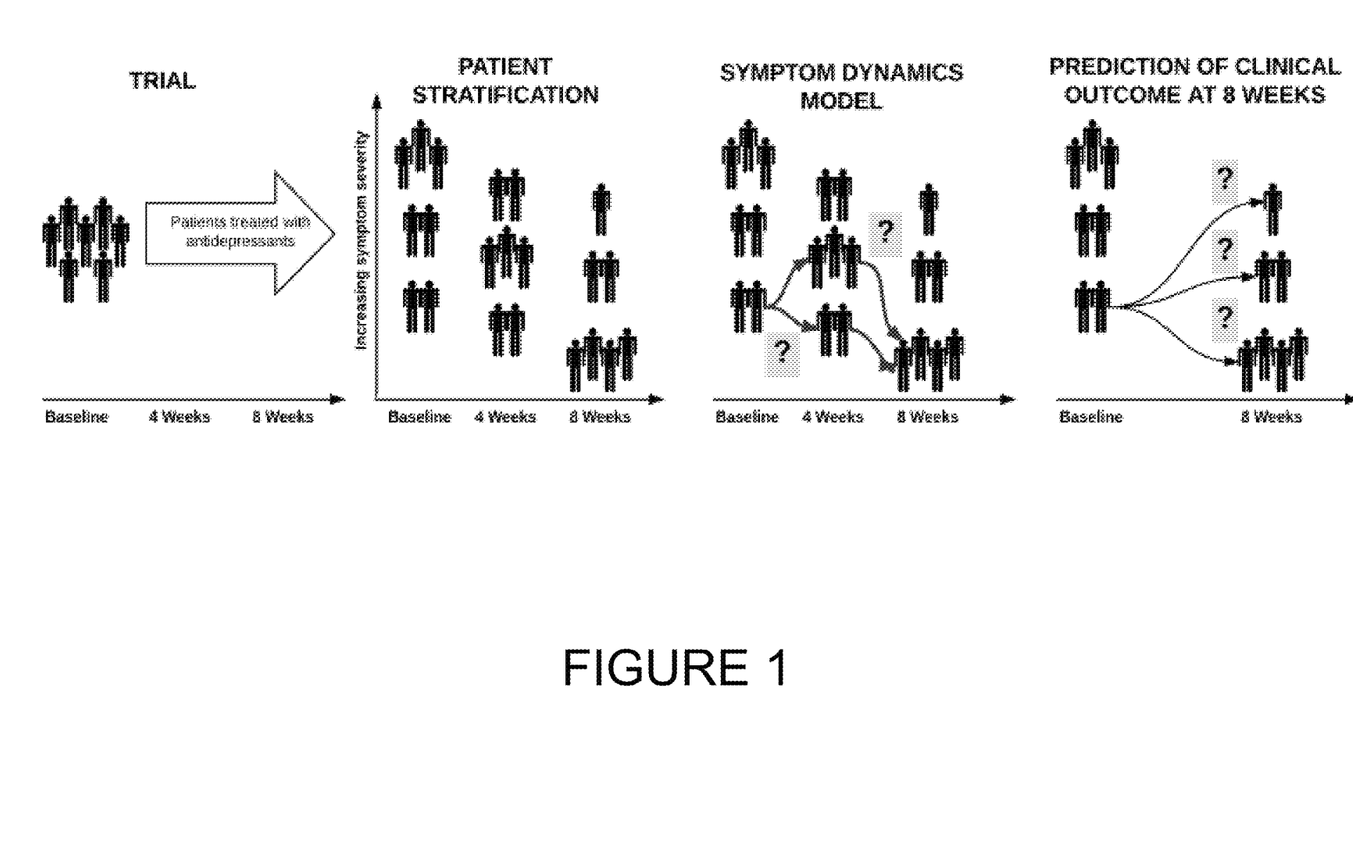
FIG. 1 illustrates an example model of symptom progression over time and across a population.

The methods described herein include receiving one or more symptom measures for a person, each symptom measure corresponding to a severity of a symptom of a disease or disorder of the person (e.g., major depressive disorder) at respective different points in time (e.g., a pre-treatment baseline point in time, a point in time two weeks post-treatment). The symptom measures are then used to predict the person's future response (e.g., the person's response, at eight weeks post-treatment, to receiving anti-depressants according to a dosing regimen) and/or to determine some other clinical course of action (e.g., to adjust a dosage of an anti-depressant or other drug, to change a drug received by the person, to select a drug from an enumerated list of potential drugs, to provide a surgery or other therapy). This is illustrated in FIG. 1, which illustrates sub-populations of patients at each of three different points in time (baseline/pre-treatment, four weeks post-treatment, and eight weeks post-treatment), and how individuals in each of the sub-populations may progress, with respect to symptom severity, from one point in time to the next.

The symptom measures can be any measure of the severity of one or more symptoms of a disease or disorder of a person. For example, the symptom measure could be a measure of the severity of major depressive disorder measured, e.g., by applying a standard clinical assessment of major depressive disorder (e.g., by having a clinician apply the Quick Inventory of Depressive Symptomatology (QIDS-C) to the person in a clinical setting). In another example, the symptom measure could be a measure of the severity of bipolar disorder. In yet another example, the symptom measure could be a measure of the severity of rheumatoid arthritis (e.g., measured using the rheumatoid arthritis severity scale (RASS)). In a further example, the symptom measure could be a measure of the severity of migraines experiences by the person (e.g., a self-reported measure of the frequency, duration, and/or severity of the migraines). In yet another example, the symptom measure could be a measure of the severity of hypertension (e.g., a measured systolic and/or diastolic blood pressure). The symptom measure could be a subjective measure (e.g., based on a patient's self-reporting, e.g., according to a Likert scale) and/or an objective measure (e.g., a galvanic skin response or other measure of physiological stress, a diastolic and/or systolic blood pressure).

Each symptom measure is then used to determine a corresponding symptom class for a set of symptom classes. That is, each symptom measure is discretized according to its corresponding point in time, with each point in time having its own respective set of symptom classes from which a symptom class may be selected for a corresponding symptom measure. Each time period for which a symptom measure is obtained (e.g., pre-treatment, two weeks post-treatment, four weeks post-treatment, between three weeks and five weeks post-treatment) has a corresponding set of symptom classes, and each symptom class corresponds to a respective range of observed symptom measure values. The symptom classes for a particular point in time may correspond to clinical populations. For example, the set of symptom classes corresponding to a pre-treatment point in time may correspond to patients exhibiting high, medium, and low levels of pre-treatment symptom severity. In another example, the set of symptom classes corresponding to a post-treatment point in time (e.g., a point in time eight weeks post-treatment) may correspond to patients that exhibit no response, response, and remission.

Thus, determining a symptom class for an observed symptom measure includes, based on the observed symptom value, selecting a symptom class from a set of symptom classes for the point in time the corresponds to the observed symptom measure. In some examples, this could include comparing the observed symptom measure to a set of symptom ranges, where each symptom range corresponds to a respective symptom class. The symptom range that contains the observed symptom measure could be determined and the corresponding symptom class selected for the observed symptom measure.

Figure 2:
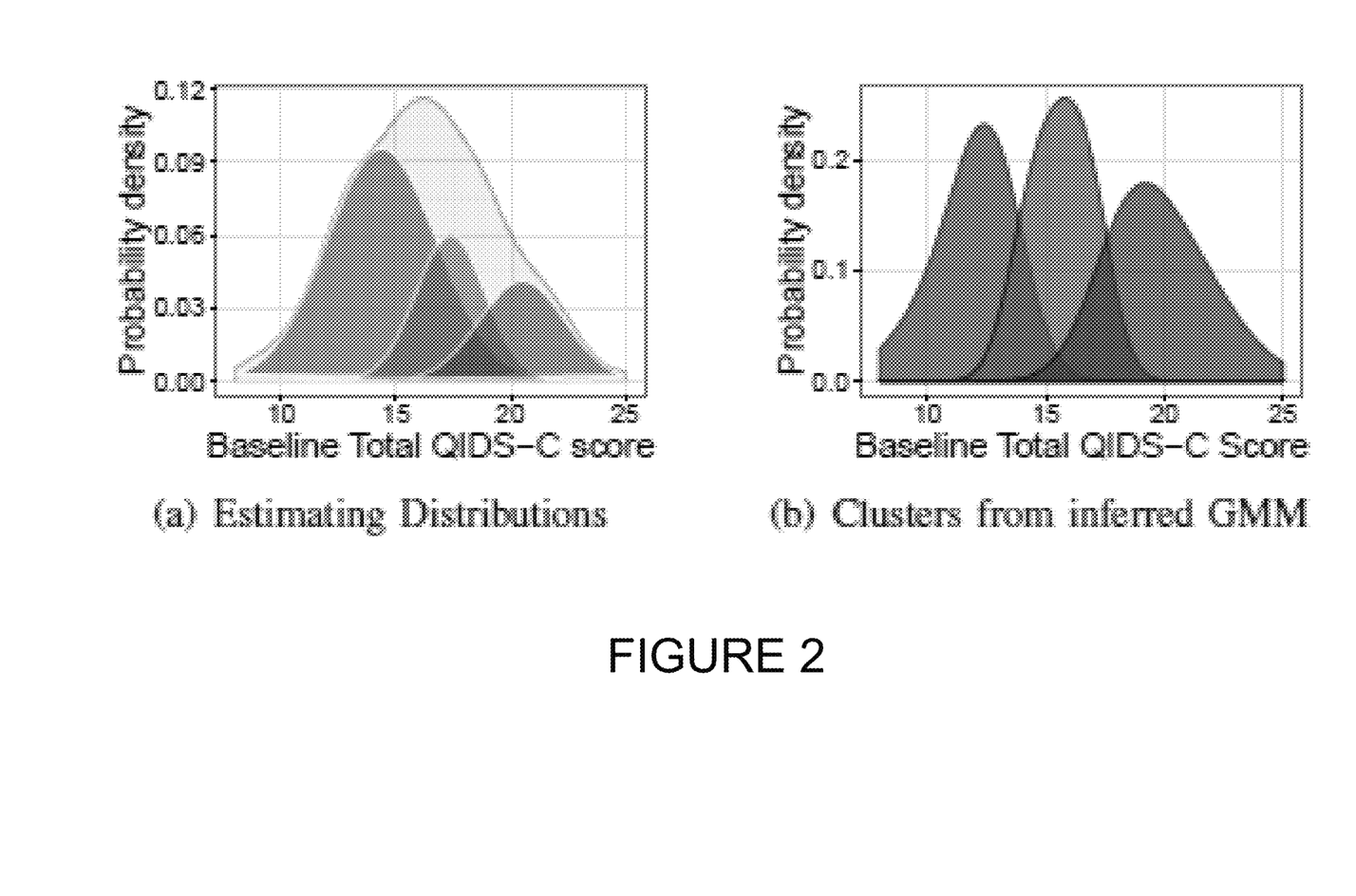
FIG. 2 illustrates example distributions of symptom severity scores and a mixed distribution thereof.

The set of symptom classes and corresponding symptom ranges for a particular point in time could be determined in a variety of ways. For example, a Gaussian mixture model (GMM) could be applied to identify sub-populations within the observed symptom measures for a given point in time. This is illustrated by FIG. 2, which shows (in light green) the overall distribution of observed symptom severity measures (of major depressive disorder, measured using the QIDS-C) at a pre-treatment point in time ("baseline"). This population contains a number of patient sub-populations, each distributed according to a respective different Gaussian distribution (illustrated in dark green, blue and purple). A Gaussian mixture model, or some other method, may be applied to the population of observed pre-treatment symptom measures in order to identify a number of symptom classes for the pre-treatment point in time. The method may also determine information about these distributions of the sub-populations corresponding to the identified symptom classes (e.g., the mean, standard deviation, etc. about the distributions). This information may then be used to determine symptom ranges or other information that could be used to determine a symptom class, from the set of symptom classes, for a particular observed symptom measure. For example, a maximum-likelihood algorithm could be applied to determine, for a particular observed symptom measure, the symptom class most likely to correspond to the particular observed symptom measure (e.g., based on the determined properties of the sub-population distributions corresponding to the symptom classes). Additionally or alternatively, such a maximum likelihood algorithm could be applied to pre-calculate symptom ranges that could then be compared to a particular observed symptom measure and to select the symptom class that corresponds to the symptom range that contains the particular observed symptom measure.

The symptom classes determined, for each observed symptom measure at each point in time for a particular person (e.g., at a single pre-treatment point in time), may then be used to generate a prediction of whether the person is likely to exhibit remission (e.g., remission of major depressive disorder at a time point between seven and nine weeks post-treatment) in response to a particular treatment (e.g., treatment with citalopram, escitalopram, or some other anti-depressant drug), to select a drug from an enumerated list of drugs that is most likely, of the drugs on the list, to result in remission and/or to minimize side effects, or to determine some other clinical course of action. This could include predicting a likely symptom measure value or class at a particular future point in time (e.g., predicting whether a person is likely to exhibit no response, to exhibit response, or to exhibit full remission in response to a treatment at a future point in time, e.g., between seven and nine weeks post-treatment).

Determining a clinical course of action could additionally or alternatively include generating a suggested change in a dosage of a drug (e.g., an anti-depressant drug being provided to the person), generating a suggested initial dose of a drug, and/or generating a suggestion that a first drug be discontinued in favor of a different drug. In another example, determining a clinical course of action could include determining that a particular surgical or other therapeutic intervention should be applied, or that the person should comply with a particular change in diet. The determined clinical course of action (e.g., the determined likelihood that a person will exhibit remission in response to a particular treatment) could then be indicated to the person and/or to a clinician, e.g., via a display or other user interface of a computer, a cellphone, a tablet, or some other system or device.

A variety of different techniques could be applied to the symptom classes in order to generate a prediction of future symptom severity (e.g., a likelihood that a person with exhibit remission) and/or some other clinical course of action. For example, an artificial neural network or other machine learning algorithm could be applied to determine the clinical course of action. Such an algorithm could be trained by a set of data that includes, for each one of a plurality of patients, observed symptom severity measures at a number of different points in time relative to a particular treatment (e.g., the prescription of an anti-depressant) as well as the eventual outcome of that treatment (e.g., a symptom severity measure at a particular point in time post-treatment, a changed dose or identity of a treatment drug). Such data could also be used to determine symptom classes and corresponding symptom ranges for each of the observed points in time. In an example, the algorithm used to determine, based on one or more symptom classes determined for a person, a clinical course of action (e.g., an estimate of whether the person is likely to exhibit remission of major depressive disorder in response to a treatment) could include a factor graph model. The application of a factor graph model to the prediction of the likelihood that a person exhibits remission, at eight weeks following treatment with an anti-depressant, is described in detail below.

Such predictive methods, based on observed symptom severity measures at different points in time pre- and/or post-treatment, could be augmented with additional information about a person. This information could include demographic information (e.g., age, level of physical activity, race, income, family history of depression or other diseases or disorders) or information about one or more physiological properties of the person, e.g., a metabolomic or genomic property of the person, a body mass index, a blood pressure, etc. A factor graph (or other algorithm) could be configured and trained to receive such information and to generate predictions of a person's future symptom severity, or to generate some other clinical course of action, based on this additional information as well as the symptom measures obtained from the person at one or more points in time (e.g., points in time relative to provision of an anti-depressant or other treatment). Genomic properties of a person could include a nucleotide sequence of the person, the presence or absence of a single-nucleotide polymorphism at a particular location within the genome of the person, or some other information about the genome or other genetic property (e.g., epigenetic markers) of the person. Metabolomic properties of a person can include levels of specified substances in the blood, lymph, saliva, tears, or other fluids of the person. Such substances of interest (e.g., in predicting response, with respect to the symptoms of major depressive disorder, to treatment with anti-depressant drugs) may include (+)-alpha-tocopherol, uric acid, kynurenine, 3-hydroxykynurenine, alpha-methyltryptophan, indole-3-propionic acid, (+)-gamma-tocopherol, serotonin, methoxy-hydroxyphenyl glycol, methionine, homogentisic acid, or 1,7-dimethylxanthine.

The methods described herein may be implemented in a variety of ways. In some examples, a cell phone, computer, tablet, or other computing device may receive, via a user interface (e.g., a touch screen, a keyboard), indications of symptom measures for a person at respective different points in time. The computing device could then, based on the received symptom measures, generate a predicted likelihood of remission or other clinical course of action and provide, via the user interface (e.g., a display), an indication of the predicted likelihood of remission and/or clinical course of action. In another example, such a device could receive, via a user interface, an indication of one or more symptom measures for a person. Such a device could operate to obtain additional symptom measures for the person (e.g., a pre-treatment symptom measure) by communicating, via a communication interface, with a remote system (e.g., medical records server) to access the additional symptom measures. In yet another example, a server could receive, from a remote device (e.g., a cell phone, a tablet, a clinician's computing device) indications of one or more symptom measures for a person at respective different points in time. The server could then, based on the received symptom measures, generate a predicted likelihood of remission or other clinical course of action. The server could then transmit an indication of the predicted likelihood of remission or other clinical course of action to the remote device. The remote device could then provide an indication (e.g., on a display) of the transmitted predicted likelihood of remission or other clinical course of action.

III. EXPERIMENTAL RESULTS

Static symptom severity measures from the three time-points of a trial were integrated into a factor graph model that captured the dynamics of the symptoms with respect to time. This factor graph model was also able to represent relationships between the symptoms and social, demographic, and metabolomics data. Factor graphs can provide a compact expressive representation of random variables and may be configured to subsume Bayesian networks, Markov random fields (MRFs) and hidden Markov models. This modeling experiment used data (603 patients×65 variables collected across three time-points) from the Mayo PGRN-AMPS clinical trial. Data from the STAR*D trial (with 1,800 patients) were used for validation of findings from the Mayo PGRN-AMPS trial.

FIG. 1 illustrates the experimental analyses used to study symptom dynamics and predictability of clinical outcomes across 8 weeks. The methods described herein (termed ALMOND) proved to be effective in 1) identifying novel biomarkers for metformin (drug) response in triple-negative breast cancer using single-cell transcriptomics data; and 2) predicting efficacy of antidepressant treatments in patients with major depressive disorder using clinical trial data of over 1,000 patients.

Data-driven analytics using factor graphs and a variety of learning methods as described herein established consistent stratification of patients and predicted symptom dynamics in depressed patients treated with antidepressants. These findings comported with existing definitions of psychiatric outcomes. Furthermore, addition of biological measures such as metabolomics and genomic properties to baseline social, demographic and clinical data significantly improved predictability in clinical outcomes at eight weeks. Top predictors identified using the methods described herein were significantly different in men and women, and correlated to metabolomic pathways of interest to the psychiatric community.

Model-based unsupervised learning identified, using the methods described herein, three distinct clusters of men and women at all three time-points represented by the Mayo PGRN-AMPS trial data based on their overall symptom severity. The clusters were not subject to variations in the subjective evaluation of specific symptoms in the questionnaire used to assess symptom severity. This clustering behavior was also observed in the STAR*D trial data. The relevance of the clustering behavior is seen at 8 weeks, at which point the three clusters comprised, respectively, all patients who 1) achieved remission, 2) demonstrated response but not remission, or 3) demonstrated no response and no remission. These functional descriptions of the identified groups broadly comport with the existing definitions of potential clinical outcomes in psychiatry.

A longitudinal factor graph was created to model the relationships (e.g., represented by factor functions of the factor graph) between clusters of patients at different time-points of the trial and associated variables (e.g., clinical outcomes, metabolomics, demographic data). The generalized factor graph can be reduced into a hidden Markov model (HMM) such that, for a given level of pre-treatment symptom severity, the forward algorithm of the HMM established the symptom dynamics.

The experimental outcomes illustrated here demonstrate that, for both types of observed clinical outcome (response and remission), the addition of baseline metabolomics data to the social, demographic, and clinical data significantly increased the predictability of observed clinical outcomes. The most predictive factors of the prediction model were significantly different between men and women, and these predictive factors correspond to factors of interest to clinical psychiatry. "Response" is defined as a 50% reduction in baseline symptoms as measured at 4 weeks or 8 weeks. If the total QIDS-C score measured at 8 weeks is <5, then the patient is said to have achieved "remission."

The Mayo PGRN-AMPS trial was designed to assess the clinical outcomes of adults (aged 18-84 years) with non-psychotic major depressive disorder (MDD) after 4 and 8 weeks of open-label treatment with citalopram or escitalopram and to examine metabolomic and genomic factors associated with the outcomes of such treatment. Subjects were recruited from primary and specialty care settings in and near Rochester, MN from March 2005 to May 2013. All psychiatric diagnoses were confirmed at the screening visit using modules of the Structured Clinical Interview for DSM-IV (SCID) administered by trained clinical research staff. The data D=[S:C:D] analyzed experimentally include social and demographic variables (S), clinical measures (C), and biological measures (B). These measures are tabulated in Table 1. The social and demographic data (S) were assessed only at baseline. The treatment outcomes were established using the 16-item, clinician-rated version of the QIDS-C at baseline, 4 weeks and 8 weeks; the results includes the clinical data C, which included the responses to the 16 QIDS-C questions and the total QIDS-C score of the symptom severity. The biological data included 31 metabolites from samples collected at baseline, 4 weeks, and 8 weeks. Samples were assayed on a high-performance liquid chromatography (HPLC) electrochemical coulometric array (LCECA) platform to obtain the standardized measures of concentrations of metabolites.

TABLE 1

Data (D = [S:C:B])
Total Patients: 603.
Men: Total: 222. With metabolomics: 99.
Women: Total: 381. With metabolomics: 191.

Social and demographic data (S) collected only at baseline

Age (in years)
Body mass index (BMI in kg/m$^2$)
Depression in {parents, siblings, children}
Bipolar disorder in {parents, siblings, children}
Alcohol abuse by {parents, siblings, children}
Drug abuse by {parents, siblings, children}
Seasonal pattern in symptom occurrence
History of psychotherapy
Clinical data (C)

Clinician-rated Quick Inventory of Depressive Symptomatology
(QIDS-C) questionnaire (16 questions)
QIDS-C total score
Biological data (B)

31 metabolites from the HPLC LCECA platform

Patients were stratified (grouped) based on their total QIDS-C score. The QIDS-C score is a measure of the severity of depression symptoms in patients. The patients were also stratified separately by gender.

The observed p-value, calculated according to the Shapiro-Wilk test, of the total QIDS-C score from all three time-points of the trial and in both men and women was less than the significance level ($\alpha$=0.05). This indicates that the observed symptom severity scores were not normally distributed, as the null hypothesis of the Shapiro-Wilk test (i.e., that the data are normally distributed) is rejected at the level of the observed p-value. Accordingly, the patient data was stratified/grouped using an assumption that the observed symptom severity scores were distributed according to a mixture of Gaussians (referred to as a Gaussian mixture model (GMM)). This process is illustrated in Algorithm 1.

Algorithm 1 Patient stratification

Input: x ← Total QIDS-C Scores
1: k ← 2
2: C ← ∅
3: a ← 0.05
4: p ← 0
5: while p ≤ a do
6:     {μ, σ$^2$} ← EM(x, k)
7:     x' ← generateSamples (μ, σ$^2$)
8:     p ← ks.test(x, x')
9:     if p > significanceLevel then
10:        C ← gmmCluster(μ, σ$^2$)
11:    end if
12:    k ← k + 1
13: end while
Output: C Starting with an assumption that the data have at least two components in the GMM, the expectation maximization (EM) algorithm was used to estimate the sufficient statistics parameters of the Gaussian components (mean and variance) of the GMM as shown in FIG. 2. 10000 samples were randomly drawn from the inferred distributions. The Kolmogorov-Smirnov test was then used to assess whether the distribution of the generated data was statistically similar to that of the original data. If the p-value (p) was less than a specified significance level ($\alpha$=0.05), then the null-hypothesis that the two distributions are not similar was rejected, and the number of components was increased by one. The new distribution (having the incremented-by-one number of components) was then fitted and tested for similarity. Once the minimum number of components K in the GMM was obtained for which the generated and input data's distributions are similar (at the specified significance level. Patients were then assigned to the component that maximizes the likelihood L(x) given the component's sufficient statistics, illustrated in FIG. 2 and described by $_{k \in [K]} L_k(x)$, where $L_k$ (x)=N (x, $\mu_k$, $\sigma_k^2$). This maximum likelihood formulation can be converted into a more efficient-to-compute form, e.g., into value ranges corresponding to each cluster k, where the ends of the ranges are computed using the maximum likelihood formulation (e.g., by determining the values at which the likelihood for neighboring clusters is equal).

Figure 3A:
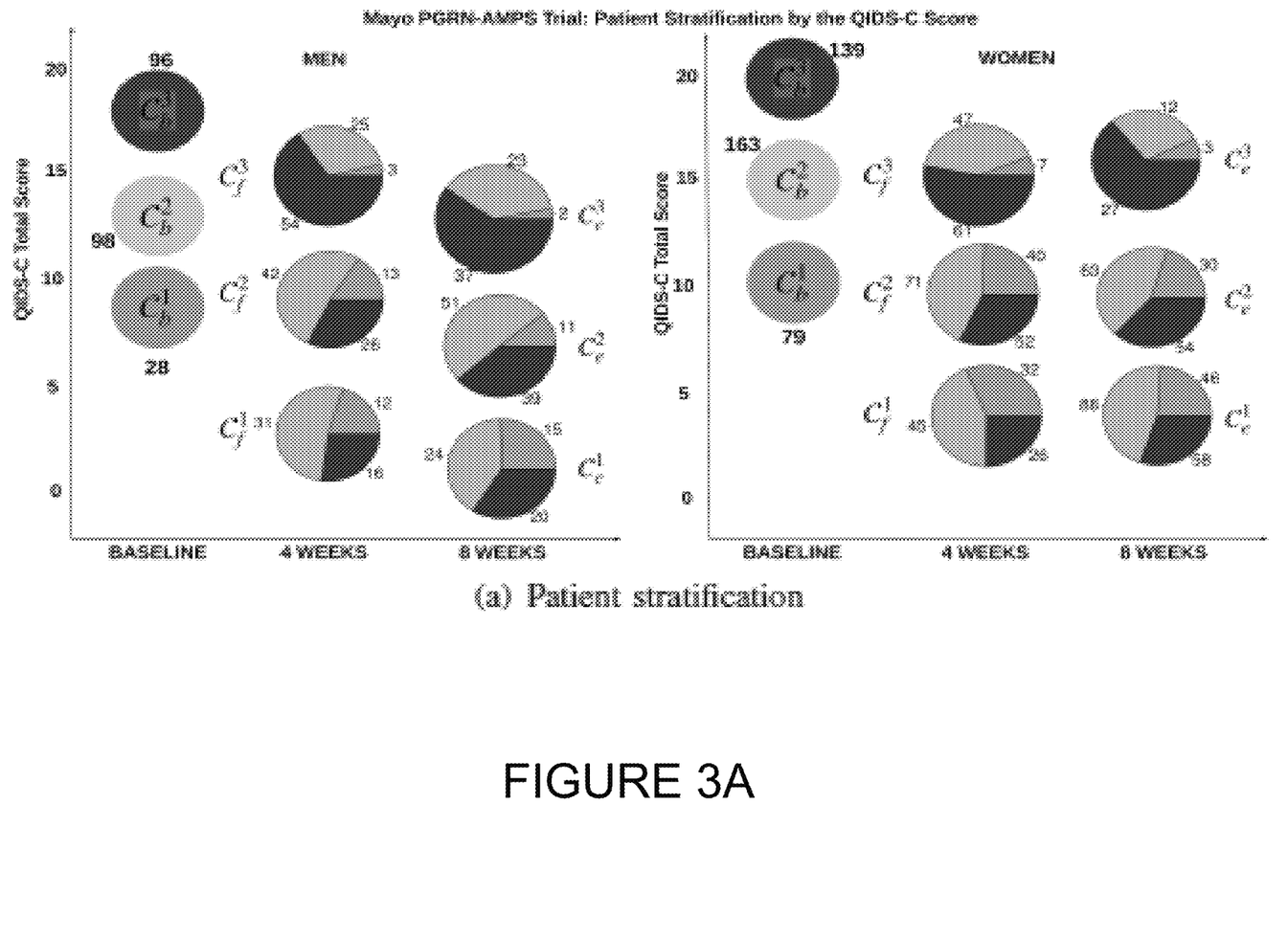
FIG. 3A illustrates the progression, over time, of symptom severity class for men and for women.

At each of the three time-points b (the baseline time point), f (the four weeks time point), and e (the eight weeks time point), three clusters of men and women were identified using the methods above. This is illustrated in FIG. 3A, which provides a pie chart for each cluster positioned at the mean of the cluster's average symptom severity score. Clusters at the baseline are $C_b = \{C_b^1, C_b^2, C_b^3\}$ at four weeks are $C_f = \{C_f^1, C_f^2, C_f^3\}$, and at eight weeks are $C_e = \{C_e^1, C_e^2, C_e^3\}$. The composition of the clusters at 4 weeks and at 8 weeks based on the baseline cluster assignments is captured in FIG. 3A. It can be seen that a significant majority of patients (96% of the 603) show reduction in their symptoms at 4 weeks and at 8 weeks. $C_e^1$ in both men and women captures all patients who achieved remission at the end of 8 weeks. $C_e^2$ in both men and women included patients who demonstrated response but did not achieve remission. $C_e^3$ in both men and women did not exhibit response or achieve remission. The same methods identified identical patient stratification when applied to the STAR*D trial (the Kolmogorov-Smirnov test for symptom severity scores between clusters of similar average symptom severity had p-value>0.08).

Figure 3B:
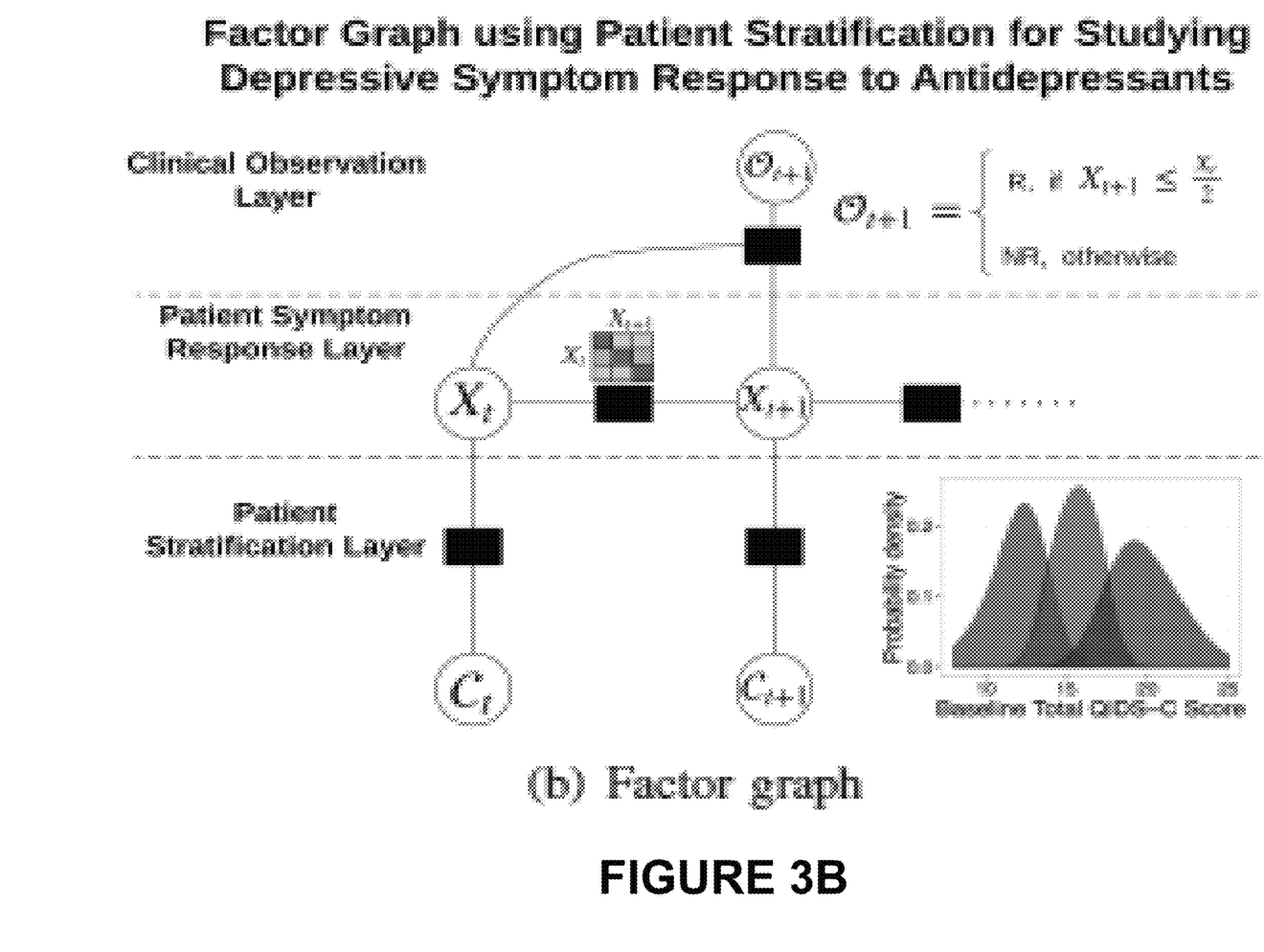
FIG. 3B illustrates the structure of an example factor graph model used herein to predict symptom severity progression over time.

Patient stratification (clusters) were obtained based only the symptom severity scores. Factor graphs were generated, for men and women separately, to model the transitions between clusters over time. A factor graph is a bipartite graph G=(V,F). The graph has three layers at each time point as illustrated in FIG. 3B; the clinical observation layer which represents clinical outcome based on observed symptom severity, the patient symptom response layer that represents changes in symptoms and the patient stratification layer that corresponds to the cluster that contains a patient's observed symptom score. Each layer is associated one variable node. Such variable nodes may include O, representing the distribution of patients who demonstrate response (R) vs no response (NR), X, representing the symptom measure at each time point, C, representing the patient stratification/clustering at each time point), and an associated factor node that may include a decision rule to determine whether a patient has demonstrated response (e.g., based on at least 50% reduction in symptom from baseline) for random variable O, a transition probability matrix for symptom severity between two time points for random variable X, and what cluster C the patient corresponds to based on his or her current symptom severity score X. The graph can be evaluated at each time point of the trial starting from baseline (t) to 4 weeks (t+1) to 8 weeks (t+2) and so on.

The forward algorithm was used to identify the most likely forward transitions a patient starting in any baseline cluster will make between clusters (hidden states C) of the trial, and also what the associated clinical outcomes are likely to be during the transitions (observed states O). During transitions between the clusters, the clinician/psychiatrist assessing the patient observes the clinical outcome $O=\{O_R, O_{NR}\}$, which is whether the patient has demonstrated either response or no-response. For both men and women, the graph with the number of patients (n), forward transitions, and observed outcomes $O=\{O_R, O_{NR}\}$ in each cluster are illustrated in FIG. 3B, which is similar to a hidden Markov model (HMM). The symptom dynamics for any patient, starting in any of the clusters at baseline, can be predicted recursively using the forward algorithm. The forward algorithm can be described as:

$$P_O(C_t) = \Sigma_{t \in T} p(O|C_t) P_O(C_{t-1}) p(C_{t-1} \to C_t)$$

where $p(O|C_t)$ is the probability of the observation (response or no-response) in a current state, $p(C_{t-1} \to C_t)$ is the probability of a transition from a state of a previous time-point to a state of the current time-point (e.g., $C_b^1 \to C_{t_f}^2$), and $P_O(C_{t-1})$ is the path probability for a given set of observations O seen until $C_{t-1}$.

Note that the reduction from a full factor graph to an HMM does not necessarily simplify the complexity of solving the forward algorithm, but may (as here) allow the symptom dynamics to be modelled not only as a function of how symptoms themselves change, but also as a function of potentially associated clinical outcomes during various time-points of the trial.

Figure 4A:
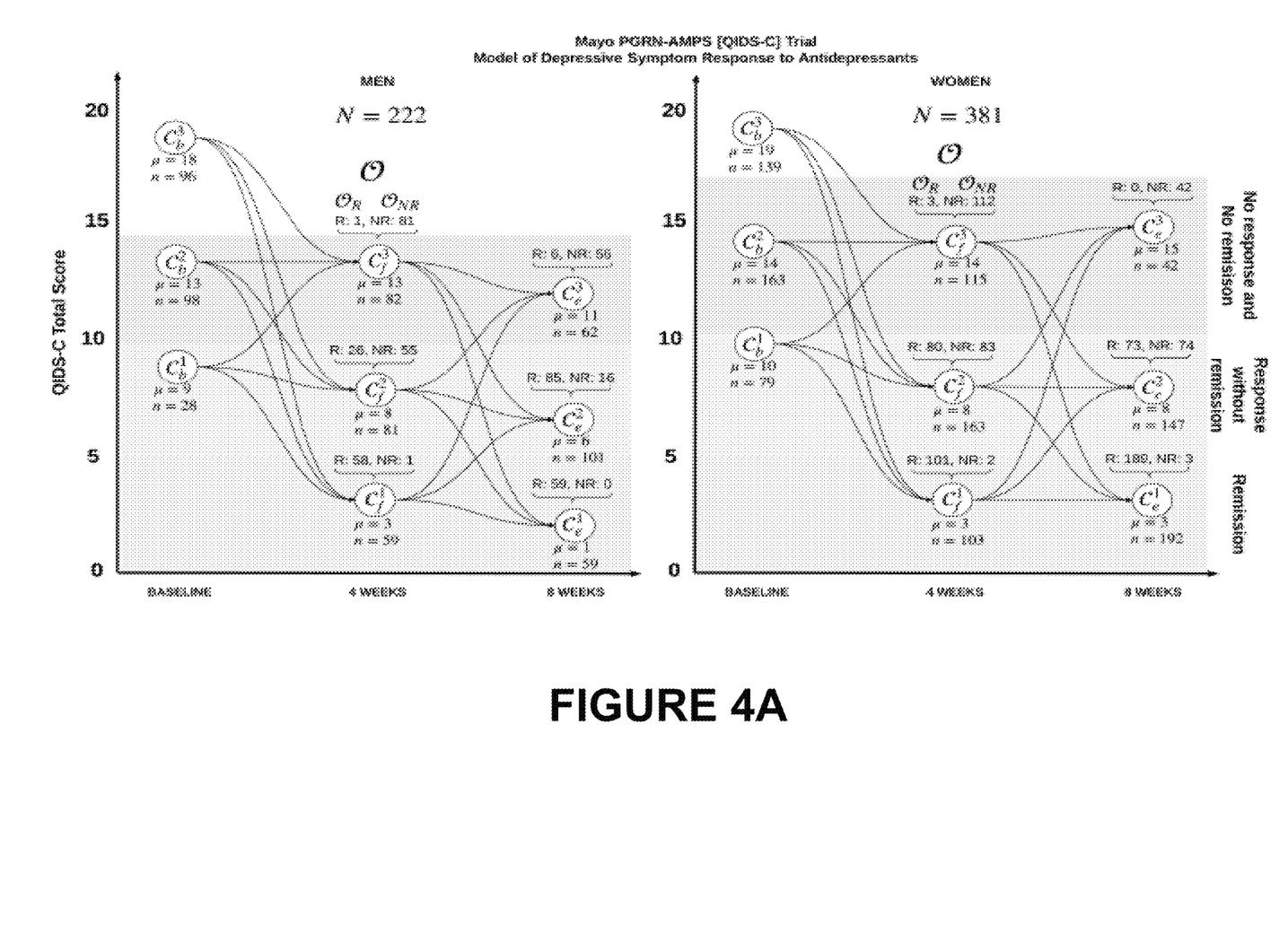
FIG. 4A illustrates experimentally observed symptom progression over time.
Figure 4B:
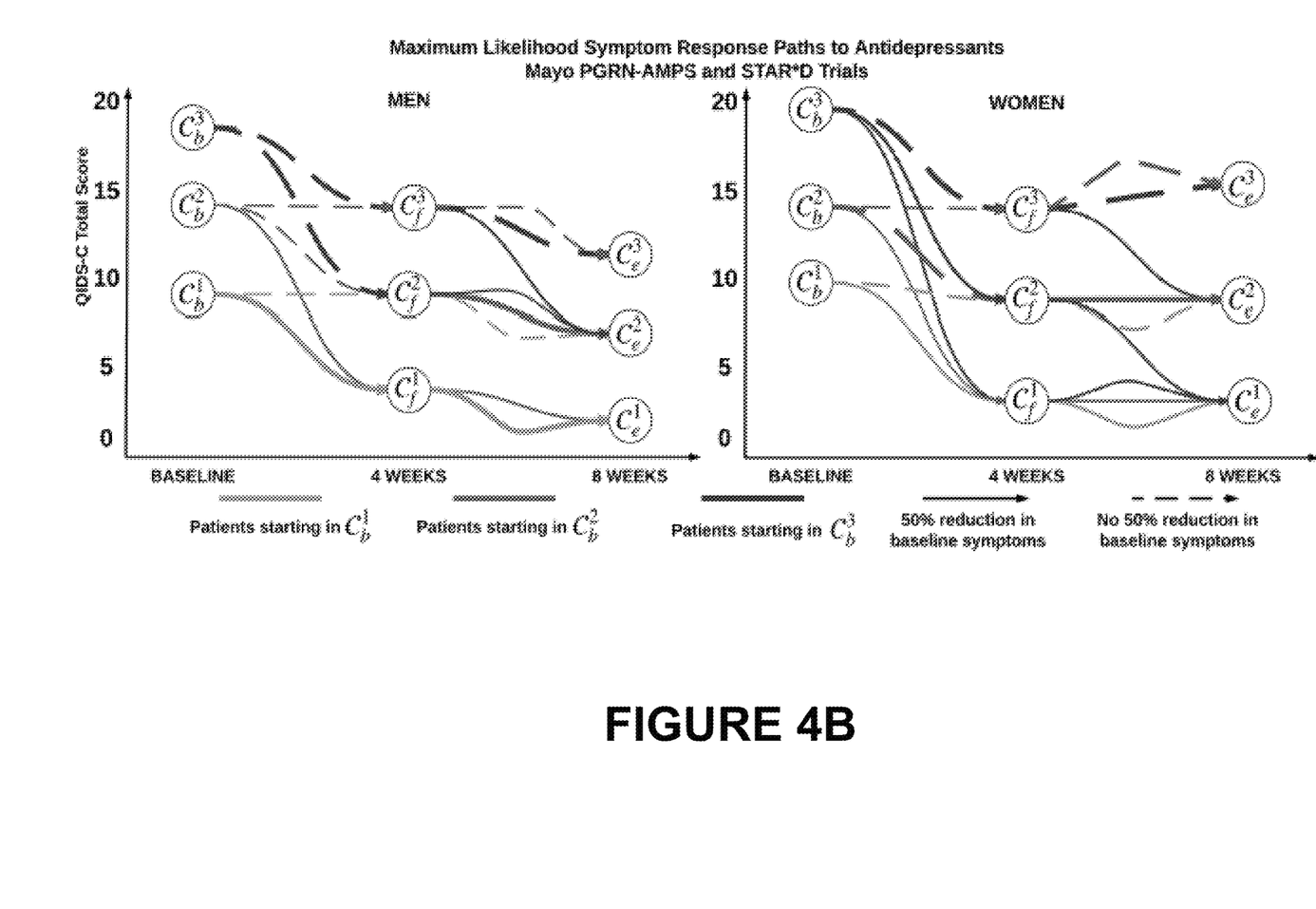
FIG. 4B illustrates predicted symptom progression over time.

For every cluster starting at the baseline, the path probabilities for all possible combination of paths and observation to the state at 8 weeks were computed using the forward equation. For each starting cluster at baseline, the path was chosen that had the highest probability of ending at each of the clusters at 8 weeks and that also included at least 20% of the cohort in the path (so that lower-probability paths are not chosen, which can lead to reduced statistical power). For example, for patients starting in $C_b^1$, the best path to $\{C_e^1, C_e^2, C_e^3\}$, was inferred and the associated outcomes that maximize the path probabilities were chosen as shown in FIGS. 4A and 4B. These results may be interpreted as follows.

A majority of the men starting in $C_b^1$ will most likely respond at 4 weeks, and they will most-likely go on to achieve remission (and thus also demonstrate response) at 8 weeks. However, if they do not respond at 4 weeks, they will likely not respond at 8 weeks either. A majority of the men starting in $C_b^2$ at baseline will most likely not respond at 4 weeks, and will also not respond at 8 weeks. However, if they respond at 4 weeks, they will likely achieve remission at 8 weeks. Men starting in $C_b^3$ at baseline are not likely to respond at 4 weeks, but two-thirds of them respond by the end of 8 weeks.

Regardless of where women start at baseline, if they respond by the end of 4 weeks, they are almost certain to achieve remission at 8 weeks. If women starting in $C_b^1$ do not respond at 4 weeks, they will likely not respond at 8 weeks either. A majority of the women starting in $C_b^2$ at baseline will most likely not respond at 4 weeks, and are more likely to respond at 8 weeks and to have moderate symptoms ($C_e^2$) than to have relatively more severe symptoms ($C_f^3$).

These fitted, validated predictive models may thus be used to predicting clinical outcomes using only baseline data. The developed factor graph for modeling symptom dynamics allows for integration of metabolomics data for each of the clusters through use of more complicated factor functions for predicting which state the patient is likely to fall into after 8 weeks of treatment. The identified clusters of patients map well to the cohorts widely acknowledged by known psychiatric definitions, such as those of responders vs non-responders ($C_e^3$ vs. the rest) and remitters vs. non-remitters ($C_e^1$ vs. the rest). The metabolomics data was collected from a smaller cohort of the Mayo PGRN-AMPS trial, which meant that some clusters included fewer than 10 patients, rendering limited statistical power. Accordingly, two binary prediction models were developed to predict 1) whether a patient will demonstrate either response or no response, and 2) whether remission or no remission will be achieved at the end of 8 weeks.

Three types of classifiers were used to perform this enhanced prediction, including kernel, linear, and ensemble methods. Support vector machines with linear kernels and support vector machines that use radial-basis kernels (SVM-RBF) were employed as the kernel methods, a generalized linear model (GLM) was employed as the linear method, and gradient-boosting machines (GBM) were employed as the ensemble method.

In addition to elastic-net regularization, recursive feature elimination (e.g., as a wrapper method) was also used for the GLM and GBM classifiers in order to estimate the model performance by not only optimizing the parameters of the model, but also by searching for an advantageous set of predictor variables. Based on the available datasets, the prediction performance did not significantly vary with or without the use of any of the feature selection methods; the prediction accuracy remained within 4%.

Tenfold cross-validation with 3 repeats and an expansive grid-search for the parameter space for the classifiers were performed in order to train the classifiers on 80% of the overall data; the remaining 20% was used for testing the trained models. A combination of the overall accuracy (i.e., the fraction of labels that were correctly predicted) and the area under the receiver operating characteristic curve (AUC) metric was used to choose the training model.

TABLE 2

Clinical outcome prediction performance for men in Mayo Clinic PGRN-AMPS trial.

| | RESPONSE | | | | | | | | |
|---|---|---|---|---|---|---|---|---|---|
| | Data | | | | | | | | |
| | Clinical Data Only | | | | Clinical and Metabolomics Data | | | | Top Predictors: GML |
| Model | SVM-RBF | SVM-Linear | GLM | GBM | SVM-RBF | SVM-Linear | GLM | GBM | ATOCO |
| Accuracy | 28.2 | 32 | 52 | 40 | 48 | 48 | 64 | 48 | URIC |
| Sensitivity | 0 | 16.67 | 16.67 | 33.33 | 33.33 | 33.33 | 50 | 33.33 | QIDS-1 |

TABLE 2-continued

Clinical outcome prediction performance for men in Mayo Clinic PGRN-AMPS trial.

| | | | | | | | | | |
|---|---|---|---|---|---|---|---|---|---|
| Specificity | 53.5 | 46.15 | 84.62 | 46.15 | 61.54 | 61.54 | 61.54 | 61.54 | KYN |
| AUC | 0.64 | 0.60 | 0.63 | 0.54 | 0.53 | 0.53 | .068 | 0.5 | 3OHKY |

REMISSION

Data

| | Clinical Data Only | | | | Clinical and Metabolomics Data | | | Top Predictors: SVM-Linear |
|---|---|---|---|---|---|---|---|---|
| Model | SVM-RBF | SVM-Linear | GLM | GMB | SVM-RBF | SVM-Linear | GLM | GBM AMTRP |
| Accuracy | 28 | 44 | 44 | 48 | 64 | 68 | 64 | 45.65 I3PA |
| Sensitivity | 38.46 | 38 | 53.85 | 46.15 | 76.52 | 76 | 76.92 | 65.22 Drug dosage |
| Specificity | 16.67 | 50 | 33.33 | 50 | 50 | 50 | 50 | 26.09 GTOCO3 |
| AUC | 0.8 | 0.6 | 0.67 | 0.6 | 0.76 | 0.78 | 0.62 | 0.6 5HT |

Abbreviations of the top predictors: ATOCO is (+)-alpha-Tocopherol; URIC is Uric acid; QIDS-1 is sleep-onset insomnia; KYN is Kynurenine; 3OHKY is 3-Hydroxykynurenine; AMTRP is Alpha-methyltryptophan; I3PA is Indole-3-propionic acid; GTOCO3 is (+)-gamma-Tocopherol (redox state #3); 5HT is serotonin.

To quantitatively assess the benefit of biological measures in predicting clinical outcomes, classifiers were trained using 1) baseline clinical data that included only social and demographic data, X=[S:C]; and 2) all baseline data (including metabolomics data), X=[S:C:B]. Metabolites whose baseline concentrations were correlated with the symptom severity at 8 weeks were chosen, and then normalized along with clinical and demographic data in order to train the chosen supervised learning methods. For all the classifiers, the AUC was compared, in addition to the generalized prediction accuracies, to see if the same model's predictive ability improved with the addition of metabolomics data. Further, if the predictability improved, the top five predictors of the model that provided the best balance of accuracy and AUC were extracted to see if the top predictors were dominated by the metabolomics.

As shown in Tables 2 and 3, for both men and women and for both outcomes response and remission, at least 3 of the 4 methods showed an improvement of the AUC and the corresponding overall accuracy, i.e., the proportion of samples correctly predicted with the addition of the metabolomics data. The highlighted columns in Tables 2 and 3 indicate the best-performing models with the metabolomics data included; 4 out of the 5 predictors are metabolites, indicating that their addition to the prediction model likely explains the increase in the predictability of the outcomes. Top predictor metabolites were also different in men and women, pointing to likely different biological mechanisms in how men and women respond to the same antidepressant.

TABLE 3

Clinical outcome prediction performance for women in Mayo Clinic PGRN-AMPS trial.

RESPONSE

Data

| | Clinical Data Only | | | | Clinical and Metabolomics Data | | | Top Predictors: SVM-Linear & GLM |
|---|---|---|---|---|---|---|---|---|
| Model | SVM-RBF | SVM-Linear | GLM | GBM | SVM-RBF | SVM-Linear | GLM | GBM Seasonal Pattern |
| Accuracy | 52.08 | 52.08 | 54.17 | 50 | 41.3 | 72.33 | 64.58 | 41.67 5HT |
| Sensitivity | 18.18 | 18.18 | 27.27 | 18.18 | 34.78 | 18.18 | 36.36 | 0 MHPG |
| Specificity | 80.72 | 80.76 | 76.92 | 76.9 | 47.83 | 92.83 | 88.46 | 76 MET |
| AUC | 0.60 | 0.59 | 0.63 | 0.63 | 0.69 | 0.74 | 0.68 | 0.49 QIDS-13 |

REMISSION

Data

| | Clinical Data Only | | | | Clinical and Metabolomics Data | | | Top Predictor: SVM-Linear |
|---|---|---|---|---|---|---|---|---|
| Model | SVM-RBF | SVM-Linear | GLM | GBM | SVM-RBF | SVM-Linear | GLM | GBM 5HT |
| Accuracy | 34.78 | 50 | 45.65 | 36.96 | 41.3 | 54.33 | 52.17 | 45.65 HGA |
| Sensitivity | 26.09 | 65.22 | 56.52 | 47.83 | 34.78 | 56.52 | 76.92 | 65.22 3OHKY |

TABLE 3-continued

Clinical outcome prediction performance for women in Mayo Clinic PGRN-AMPS trial.

| | | | | | | | | | |
|---|---|---|---|---|---|---|---|---|---|
| Specificity | 43.48 | 34.78 | 34.78 | 26.09 | 47.83 | 52.17 | 50 | 26.09 | Seasonal Pattern PARAXAN |
| AUC | 0.64 | 0.48 | 0.42 | 0.58 | 0.56 | 0.53 | 0.53 | 0.47 | |

Abbreviations of the top predictors: 5HT is Serotonin; MHPG is Methoxy-Hydroxyphenly Glycol; MET is Methionine; QIDS-13 is involvement; HGA is Homogentisic Acid; 3OHKY is 3-Hydroxykynurenine; PARAXAN is 1,7-diMethylxanthine.

Patient stratification consistency, correlating to known psychiatric definitions of outcomes and replicated in both the Mayo PGRN-AMPS and STAR*D trial, provided a show of confidence in modeling symptom responses to citalopram/escitalopram (antidepressant) treatment in depressed patients. The factor graph model was able to show potentially important clinical differences between men and women in depressive symptom behavior over time under antidepressant treatment. Emphasis in this work on remission, which is defined clinically as a relative absence of depressive symptoms, was motivated by the fact that failure to achieve remission is associated with ongoing difficulties with psychosocial functioning owing to residual depressive symptoms, and higher odds of full depressive relapses, even for patients who achieve a positive response. For women, achieving response to antidepressant treatment at 4 weeks strongly predicted remission at 8 weeks regardless of baseline depressive symptom severity. For men, the same was also true, but only for those in the low ($C_b^1$) and moderate ($C_b^2$) symptom clusters at baseline. In those groups, failure to achieve response at 4 weeks was highly predictive of a lack of remission at 8 weeks, with the only exception being for men in the most severe symptom cluster at baseline ($C_b^3$). In that group of men with more severe depression at baseline, the odds of response at 4 weeks were low; however, two-thirds of these individuals either responded or remitted by week 8. In general, these results support the prevailing clinical recommendation to examine depressive symptoms after 4-6 weeks of treatment before judging the clinical effects of antidepressant treatment. These results suggest that ascertaining clinical effects of an antidepressant at 4 weeks may be especially reasonable for women, regardless of their baseline symptom severity, and for men with milder-to-moderate depressive symptoms at baseline. For men with more severe depression at the start of treatment, the time window may need to be extended beyond 4 weeks before the full effects of treatment with antidepressant at a given dose can be judged.

The results of this work indicated an overall improvement in the accuracy of predictions when incorporating metabolomics data. Additionally, metabolites known to be implicated in psychiatric effects were found to be among the top predictors of the outcomes. Specifically, for decades the treatment of MDD has focused on biogenic amine neurotransmitter pathways, i.e., the synthesis and metabolism of catecholamines such as norepinephrine and indoleamines such as serotonin. Indeed, the metabolites listed in Tables 2 and 3 include serotonin (5HT) itself as well as two metabolites from the competing tryptophan metabolism pathway (KYN and 3OHKYN) and the major catecholamine metabolite (MHPG), which are known to play a role in behavioral sciences.

IV. CONCLUSION

The invention is not intended to be limited to the disclosed embodiments of the invention. It should be understood that the foregoing disclosure emphasizes certain specific embodiments of the invention and that all modifications or alternatives equivalent thereto are within the spirit and scope of the invention as set forth in the appended claims The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A method comprising:
    obtaining a first symptom measure for a person, wherein the first symptom measure corresponds to a severity of major depressive disorder at a first point in time;
    based on the first symptom measure, selecting a first symptom class from a first set of symptom classes, wherein selecting the first symptom class comprises determining which symptom range of a first set of symptom ranges contains the first symptom measure and selecting the symptom class, from the first set of symptom classes, that corresponds to the determined symptom range;
    obtaining at least one of a metabolomic property or a genomic property of the person;
    selecting, based on the first symptom class and the at least one of a metabolomic property or a genomic property of the person, a drug from an enumerated list of drugs for a treatment of major depressive disorder; and
    providing the selected drug to the person.

2. The method of claim 1, further comprising:
    obtaining at least one of an age or a body mass index of the person;
    wherein selecting a drug from the enumerated list of drugs for the treatment of major depressive disorder comprises selecting the drug from the enumerated list of drugs based on the obtained age or body mass index.

3. The method of claim 1, wherein obtaining at least one of a metabolomic property or a genomic property of the person comprises obtaining a baseline blood concentration, in the person, of at least one of (+)-alpha-tocopherol, uric acid, kynurenine, 3-hydroxykynurenine, alpha-methyltryptophan, indole-3-propionic acid, (+)-gamma-tocopherol, serotonin, methoxy-hydroxyphenyl glycol, methionine, homogentisic acid, or 1,7-dimethylxanthine.

4. The method of claim 1, further comprising:
obtaining a second symptom measure for the person, wherein the second symptom measure corresponds to a severity of major depressive disorder at a second point in time, wherein the second point in time is subsequent to the first point in time;
based on the second symptom measure, selecting a second symptom class from a second set of symptom classes, wherein selecting the second symptom class comprises determining which symptom range of a second set of symptom ranges contains the second symptom measure and selecting the symptom class, from the second set of symptom classes, that corresponds to the determined symptom range;
wherein selecting a drug from the enumerated list of drugs for the treatment of major depressive disorder comprises selecting the drug from the enumerated list of drugs based on the selected second symptom class.

5. The method of claim 4, wherein the first point in time and the second point in time are separated in time by between three weeks and five weeks.

6. The method of claim 1, wherein obtaining the first symptom measure comprises operating a communications interface of a server to receive an indication of the first symptom measure from a remote device, wherein the method further comprises:
transmitting an indication of the selected drug to the remote device.

7. The method of claim 1, further comprising:
determining a dosage of the selected drug based on the first symptom class and the at least one of a metabolomic property or a genomic property of the person, wherein providing the selected drug to the person comprises providing the selected drug to the person at the determined dosage.

8. The method of claim 1, wherein the enumerated list of drugs for the treatment of major depressive disorder includes citalopram and escitalopram.

9. A method comprising:
obtaining a first symptom measure for a person, wherein the first symptom measure corresponds to a severity of major depressive disorder at a first point in time;
based on the first symptom measure, selecting a first symptom class from a first set of symptom classes, wherein selecting the first symptom class comprises determining which symptom range of a first set of symptom ranges contains the first symptom measure and selecting the symptom class, from the first set of symptom classes, that corresponds to the determined symptom range;
obtaining a second symptom measure for the person, wherein the second symptom measure corresponds to a severity of major depressive disorder at a second point in time, wherein the second point in time is subsequent to the first point in time;
based on the second symptom measure, selecting a second symptom class from a second set of symptom classes, wherein selecting the second symptom class comprises determining which symptom range of a second set of symptom ranges contains the second symptom measure and selecting the symptom class, from the second set of symptom classes, that corresponds to the determined symptom range;
selecting, based on the first symptom class and the second symptom class, a drug from an enumerated list of drugs for a treatment of major depressive disorder; and
providing the selected drug to the person.

10. The method of claim 9, further comprising:
obtaining at least one of an age or a body mass index of the person;
wherein selecting a drug from an enumerated list of drugs comprises selecting the drug from an enumerated list of drugs based on the obtained age or body mass index.

11. The method of claim 9, further comprising:
obtaining at least one of a metabolomic property or a genomic property of the person;
wherein selecting a drug from an enumerated list of drugs comprises selecting the drug from an enumerated list of drugs based on the obtained metabolomic property or genomic property.

12. The method of claim 11, wherein obtaining at least one of a metabolomic property or a genomic property of the person comprises obtaining a baseline blood concentration, in the person, of at least one of (+)-alpha-tocopherol, uric acid, kynurenine, 3-hydroxykynurenine, alpha-methyltryptophan, indole-3-propionic acid, (+)-gamma-tocopherol, serotonin, methoxy-hydroxyphenyl glycol, methionine, homogentisic acid, or 1,7-dimethylxanthine.

13. The method of claim 9, further comprising:
obtaining a third symptom measure for the person, wherein the third symptom measure corresponds to a severity of major depressive disorder at a third point in time, wherein the third point in time is subsequent to the second point in time;
based on the third symptom measure, selecting a third symptom class from a third set of symptom classes, wherein selecting the third symptom class comprises determining which symptom range of a third set of symptom ranges contains the third symptom measure and selecting the symptom class, from the third set of symptom classes, that corresponds to the determined symptom range;
wherein selecting a drug from an enumerated list of drugs comprises selecting the drug from an enumerated list of drugs based on the determined third symptom class.

14. The method of claim 9, wherein the first point in time and the second point in time are separated in time by between three weeks and five weeks.

15. The method of claim 9, wherein selecting a drug from an enumerated list of drugs comprises determining a predicted symptom measure for the person that corresponds to a severity of major depressive disorder of the person at between seven weeks and nine weeks after the first point in time if the person was treated with the selected drug.

16. The method of claim 9, wherein selecting a drug from an enumerated list of drugs comprises applying the first symptom class and the second symptom class to a factor graph model to select the drug from an enumerated list of drugs.

* * * * *